United States Patent
Wake et al.

(10) Patent No.: US 6,571,116 B2
(45) Date of Patent: May 27, 2003

(54) MEDICAL OPTICAL IMAGING SCANNER USING MULTIPLE WAVELENGTH SIMULTANEOUS DATA ACQUISITION FOR BREAST IMAGING

(75) Inventors: Robert H. Wake, Cooper City, FL (US); Richard J. Grable, Plantation, FL (US)

(73) Assignee: Imaging Diagnostic Systems, Inc., Plantation, FL (US)

( * ) Notice: Subject to any disclaimer, the term of this patent is extended or adjusted under 35 U.S.C. 154(b) by 0 days.

(21) Appl. No.: 09/851,437

(22) Filed: May 9, 2001

(65) Prior Publication Data

US 2002/0045833 A1 Apr. 18, 2002

Related U.S. Application Data

(60) Provisional application No. 60/202,933, filed on May 9, 2000.

(51) Int. Cl.[7] .................................................. A61B 6/00
(52) U.S. Cl. .................................................. 600/431
(58) Field of Search ............................... 100/431, 432, 100/433, 434, 435, 407; 250/302; 424/1, 4

(56) References Cited

U.S. PATENT DOCUMENTS

| 5,491,627 | A | * | 2/1996 | Zhang et al. ............... 600/408 |
|---|---|---|---|---|
| 5,800,350 | A | * | 9/1998 | Coppleson et al. .......... 600/372 |
| 5,876,339 | A | | 3/1999 | Lemire |
| 5,963,658 | A | * | 10/1999 | Klibanov et al. ........... 382/128 |
| 6,044,288 | A | | 3/2000 | Wake et al. |
| 6,175,759 | B1 | | 1/2001 | Chan et al. |
| 6,280,386 | B1 | | 8/2001 | Alfano et al. |
| 6,356,782 | B1 | * | 3/2002 | Sirimanne et al. .......... 600/431 |
| 6,377,838 | B1 | * | 4/2002 | Iwanczyk et al. ........... 600/425 |
| 6,397,099 | B1 | * | 5/2002 | Chance ....................... 600/473 |
| 6,415,172 | B1 | * | 7/2002 | Painchaud et al. .......... 600/407 |
| 6,490,470 | B1 | * | 12/2002 | Kruger ........................ 600/407 |

FOREIGN PATENT DOCUMENTS

| EP | 569 238 | * | 10/1993 |
| JP | 06054843 | * | 3/1994 |

* cited by examiner

Primary Examiner—Teresa Walberg
Assistant Examiner—Daniel Robinson
(74) Attorney, Agent, or Firm—Shlesinger, Arkwright & Garvey LLP

(57) ABSTRACT

A scanner for a medical optical imaging device, comprises an illumination source positioned to direct emitted light into a breast positioned below a support surface; first and second groups of photodetectors positioned in an arc around the breast to simultaneously detect light emerging from the breast; and optical filters disposed in front of the first group of photodetectors to restrict the wavelength of light reaching the first group of photodetectors.

8 Claims, 6 Drawing Sheets

US 6,571,116 B2

MEDICAL OPTICAL IMAGING SCANNER USING MULTIPLE WAVELENGTH SIMULTANEOUS DATA ACQUISITION FOR BREAST IMAGING

RELATED APPLICATION

This is a nonprovisional application claiming the priority benefit of provisional application Ser. No. 60/202,933, filed May 9, 2000, which is hereby incorporated by reference.

FIELD OF THE INVENTION

The present invention generally relates to diagnostic medical imaging apparatus and more particularly to a mammography machine that employs a near-infrared laser as a radiation source.

BACKGROUND OF THE INVENTION

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticated, automated equipment to reliably accomplish the detection process.

The x-ray absorption density resolution of present photographic x-ray methods is insufficient to provide reliable early detection of malignant tumors. Research has indicated that the probability of metastasis increases sharply for breast tumors over 1 cm size. Tumors of this size rarely produce sufficient contrast in a mammogram to be detectable. To produce detectable contrast in photographic mammograms, 2–3 cm dimensions are required. Calcium deposits used for inferential detection of tumors in conventional mammography also appear to be associated with tumors of large size. For these reasons, photographic mammography has been relatively ineffective in the detection of this condition.

Most mammographic apparatus in use today in clinics and hospitals require breast compression techniques which are uncomfortable at best and in many cases painful to the patient. In addition, x-rays constitute ionizing radiation which injects a further risk factor into the use of mammographic techniques as most universally employed.

Ultrasound has also been suggested, as in U.S. Pat. No. 4,075,883, which requires that the breast be immersed in a fluid-filled scanning chamber. U.S. Pat. No. 3,973,126 also requires that the breast be immersed in a fluid-filled chamber for an x-ray scanning technique.

In recent times, the use of light and more specifically laser light to noninvasively peer inside the body to reveal the interior structure has been investigated. This technique is called optical imaging. Optical imaging and spectroscopy are key components of optical tomography. Rapid progress over the past decade have brought optical tomography to the brink of clinical usefulness. Optical wavelength photons do not penetrate in vivo tissue in a straight line as do x-ray photons. This phenomenon causes the light photons to scatter inside the tissue before the photons emerge out of the scanned sample.

Because x-ray photon propagation is essentially straight-line, relatively straight forward techniques based on the Radon transform have been devised to produce computed tomography images through use of computer algorithms. Multiple measurements are made through 360° around the scanned object. These measurements, known as projections, are used to back project the data to create an image representative of the interior of the scanned object.

In optical tomography, mathematical formulas and projection techniques have been devised to perform a reconstruction function somewhat similar to x-ray tomography. However, because light photon propagation is not straight-line, techniques to produce cross-section images are mathematically intensive and invariably require establishing the boundary of the scanned object. Boundary determination is important because it serves as the basis for reconstruction techniques to produce interior structure details. Algorithms to sate do not use any form of direct measurement techniques to establish the boundary of the scanned object.

Addition information concerning the interior of the breast can be obtained when a scanner is able to acquire data resulting from illuminating the breast with different wavelengths or from acquiring information pertaining to light emitted by fluorescent materials introduced into the breast.

OBJECTS AND SUMMARY OF THE INVENTION

It is an object of the present invention to provide a scanner for a medical optical imaging device that uses a fluorescent marker to provide an enhanced identification of an abnormality within the breast beyond the inherent localized changes in optical scattering and absorption.

It is another object of the present invention to provide a scanner for a medical optical imaging device that provides for simultaneous acquisition of optical data at multiple wavelengths.

It is still another object of the present invention to provide a scanner for a medical optical imaging device that provides for simultaneous acquisition of data from at least two planes within the breast.

It is another object of the present invention to provide a scanner for a medical optical imaging device that provides for simultaneous acquisition of attenuation data and fluorescence data.

It is another object of the present invention to provide a scanner for a medical optical imaging device that provides for acquiring pre- and post-injection of a contrast agent, such as Indocynine Green (ICG) of both attenuation and fluorescence data and reconstructing the image from the difference between the raw data sets.

In summary, the present invention provides a scanner for a medical optical imaging device, comprising an illumination source positioned to direct emitted light into a breast positioned below a support surface; first and second groups of photodetectors positioned in an arc around the breast to simultaneously detect light emerging from the breast; and optical filters disposed in front of the first group of photodetectors to restrict the wavelength of light reaching the first group of photodetectors.

The present invention also provides an apparatus for imaging a breast, comprising a scanning chamber for receiving therein the breast to be scanned; a laser beam disposed within the scanning chamber for impinging on the breast, the laser beam being adapted to orbit around the breast; first and second groups of detectors positioned in an arc around the breast to simultaneously detect light emerging from the breast to generate first and second projection data, respectively; optical filters operably associated with the first group of detectors to restrict the wavelength of light reaching the first group of detectors to the wavelength of radiation emitted by a contrast agent introduced into the breast after being activated by the beam; and a computer to reconstruct an image of the breast from projection data derived from subtracting first and second baseline projection data prior to introduction of the contrast agent into the breast from respective first and second projection data obtained after introduction of the contrast agent.

The present invention further provides a method for collecting data for use in image reconstruction of a breast being scanned, comprising providing a beam of laser; providing a contrast agent within the breast; orbiting the laser beam around the breast clockwise to obtain a first set of projection data; orbiting the laser beam around the breast counterclockwise to obtain a second set of projection data; providing first and second groups of detectors positioned in an arc around the breast to detect light emerging from the breast to generate the first and second sets of projection data, respectively; restricting the first group of detectors to the wavelength of radiation emitted by a contrast agent within the tissue after being activated by said laser beam; and subtracting first and second baseline projection data obtained prior to introduction of the contrast agent into the breast from respective first and second projection data obtained after the contrast agent has been introduced to obtain respective differential projection data to be used in image reconstruction.

These and other objects of the present invention will become apparent from the following detailed description.

BRIEF DESCRIPTIONS OF THE DRAWINGS

FIG. 6 is a graph showing the spectral response for the detector, laser beam, fluorescence emission wavelengths and the optical filter spectral response.

DETAILED DESCRIPTION OF THE INVENTION

A medical optical imaging device is disclosed in U.S. Pat. Nos. 5,692,511, 6,100,520, and 6,130,958, which are hereby incorporated by reference.

Figure 1:
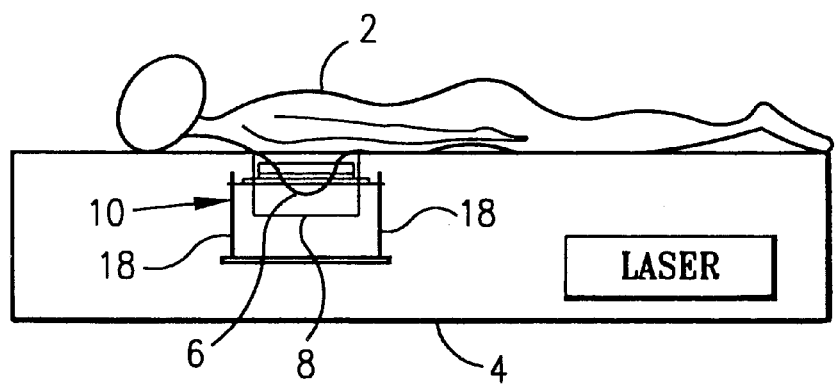
FIG. 1 is a schematic side elevational view of a medical optical imaging device showing a patient positioned on a support with her breast pendent within a scanning chamber made in accordance with the present invention.
Figure 2:
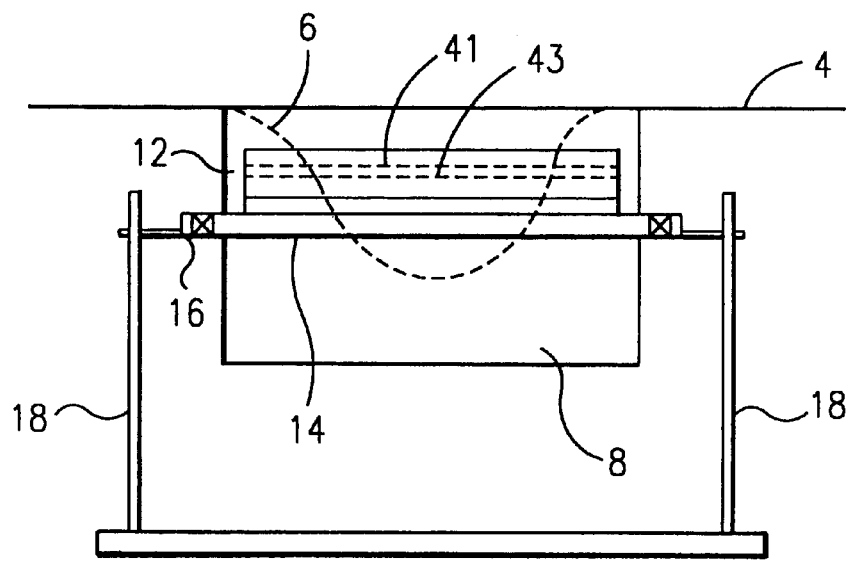
FIG. 2 is an enlarged schematic side elevational view of the scanner shown in FIG. 1.

Referring to FIGS. 1 and 2, a patient 2 is positioned prone on a scanning table 4 with one breast 6 pendulant in a scanning chamber 8 through an opening 3 through the table. A medical optical imaging scanner 10 comprises a laser beam 11 and a collimator 12 secured to an orbit plate 14 and an elevator plate 16. The collimator 12 is associated with photodetectors 22 (see FIG. 4), such as photodiodes. The orbit plate 14 is orbited through one circle around the breast to obtain a set of data. The elevator plate 16 is moved vertically by drive screws 18 to position the orbit plate 14 at different vertical locations where the orbit plate 14 is again orbited through one circle around the breast to obtain another set of data.

Figure 3:
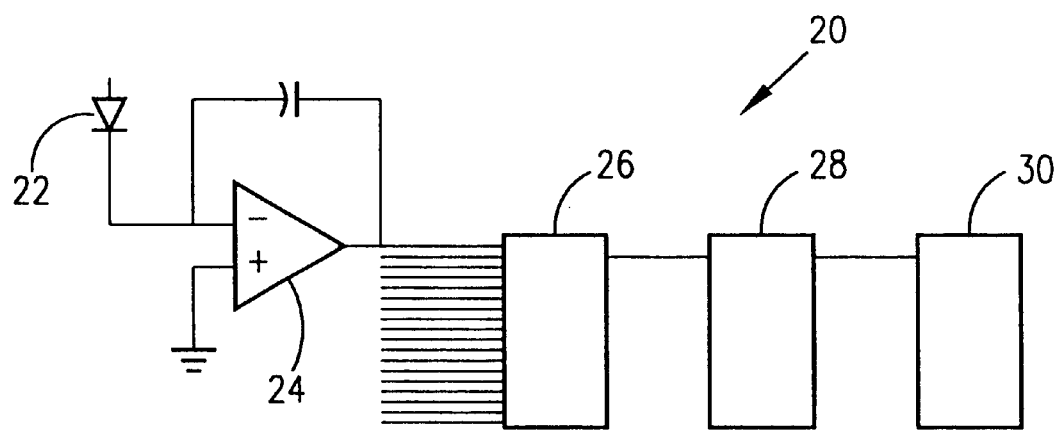
FIG. 3 is a schematic diagram of a signal processing system used in the present invention.

Referring to FIG. 3, a schematic diagram of an electronic data acquisition system 20 is disclosed. It should be understood that a number of photodetectors 22 are used, configured in an arc around the breast, although only one photodetector 22 is shown for clarity. Light impinging on photodetector 22, such as a photodiode, causes a current to flow. Each photodetector 22 is connected to its own integrator 24 which produces a voltage output proportional to the amount of current generated by the photodetector 22. The voltage output is coupled to an electronic multiplexer 26. The output of the multiplexer 26 is coupled to an analog-to-digital converter (ADC) 28 to provide a digitized output, which is coupled to a computer 30 where the digitized output is stored for future use. Examples of the system 20 are disclosed in U.S. Pat. No. 6,150,649 and co-pending application Ser. No. 09/199,440, filed Nov. 25, 1998, both of which are hereby incorporated by reference.

Figure 4:
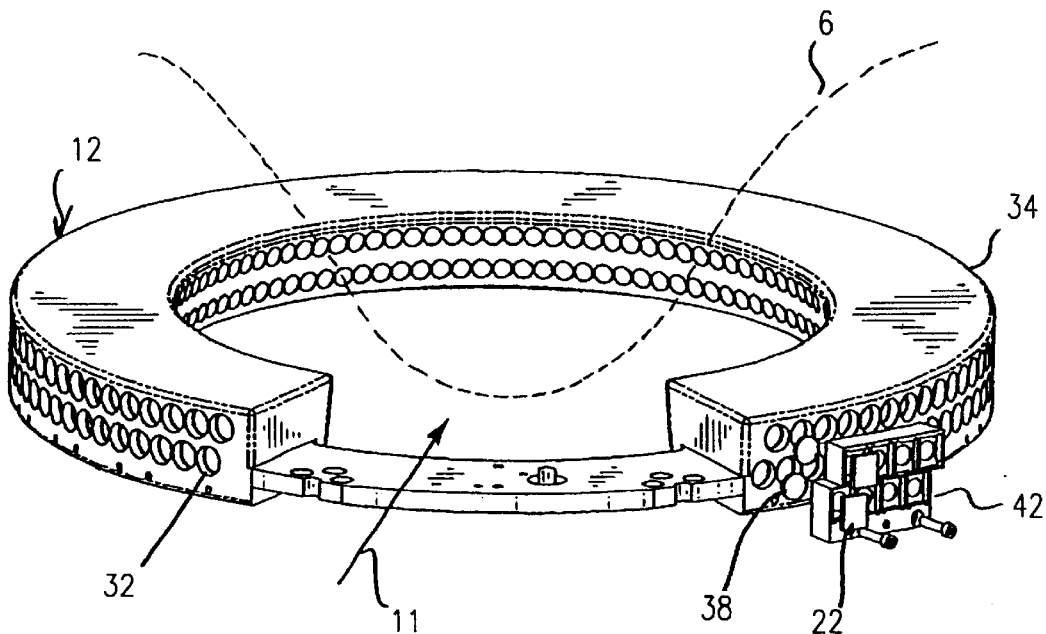
FIG. 4 is a perspective view of a collimator made in accordance with the present invention, showing a plurality of openings to restrict the field of view of detectors.

Referring to FIG. 4, the collimator 12 comprises a series of holes 32 through a body 34 that arches around the breast 6. Photodetectors 22 are positioned at the end of each hole 32 to detect light coming from the breast 6 due to the laser beam 11 impinging on the breast during scanning. A lens 38 may be placed in front of each photodetector 22 to increase light collection capability.

The collimator holes 32 are arranged into an upper row and a lower row. The horizontal centerline through each hole 32 along the upper row of holes 32 is parallel to the centerline of each hole 32 along the lower row. The centerlines for the upper row of holes define a plane 41 through the breast. The centerlines for the holes in the lower row define another plane 43. The upper row of holes The vertical center line of each hole in the upper row may be in line with the vertical center line of a corresponding hole in the lower row. Alternately, the vertical center line of each hole in the upper row may be interdigitated or horizontally offset with the vertical center line of the holes in the second row to minimize the vertical separation between the two rows.

Figure 5:
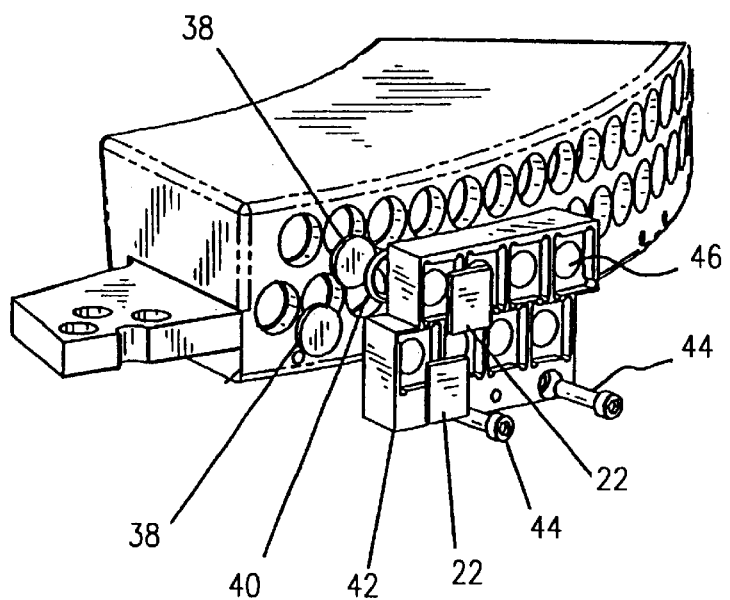
FIG. 5 is an enlarged fragmentary perspective view of a portion of the collimator shown in FIG. 4, showing the incorporation of filter for the upper row of detectors.

Referring to FIG. 5, an optical cut-off or band pass filter 40 is placed in front of each photodetector 22 associated with the upper row of holes 32 to limit the photodetector's spectral response to the desired range of wavelength. A holding block 42 is used to hold the assembly together and accurately position the photodetectors 22. Machine screws 44 hold the block 42 to the body 34. It should be understood that a number of the holding blocks 42, along with their respective photodetectors, would be used, although only one is shown for clarity. The holding block 42 has openings 46 to allow the light passing through the holes 32 to reach the respective photodetectors 22.

Figure 6:
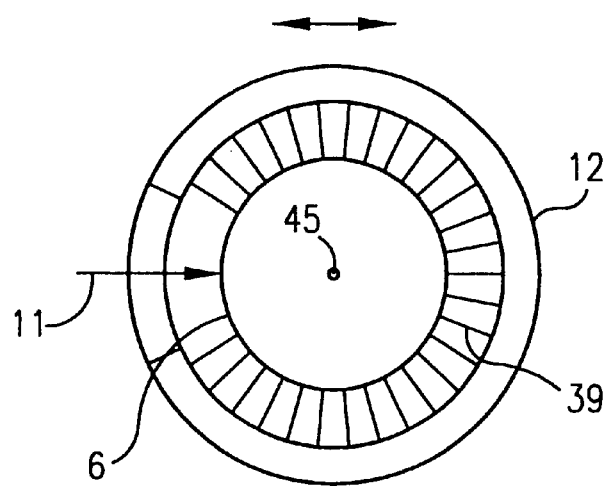
FIG. 6 is schematic plan view of the scanner, showing the relationship between the patient's breast, illumination beam, collimator, detector field of view, and the detector.

The collimator 12 is shown schematically in plan view in FIG. 6. Each opening 32 is directed to the center of rotation 45 of the scanner. Each opening 32 has a field of view, schematically indicated at 39, to restrict the amount and direction of light that can be detected by the photodetectors 22. Examples of collimators are disclosed in U.S. Pat. No. 6,100,520, which is hereby incorporated by reference.

The scanner 10 is used to simultaneously acquire data at two different wavelengths. One set of data corresponding to one wavelength is acquired by the photodetectors associated with the upper row of holes 32 and another set of data corresponding to another wavelength is acquired by the photodetectors associated with the lower row of holes 32. This is accomplished by limiting the exposure of the upper or lower row of photodetectors to certain wavelengths by means of the filter 40. The filter 40 blocks all of the light transmitted through the breast at the laser source wavelength while permitting fluorescent light to be detected. The other row of photodetectors detect the sum of the light transmitted through the breast and the fluorescent light emitted from within the breast. With this configuration, both the effective attenuation and fluorescent images maybe reconstructed from a single rotation of the scanner around the breast.

Figure 7:
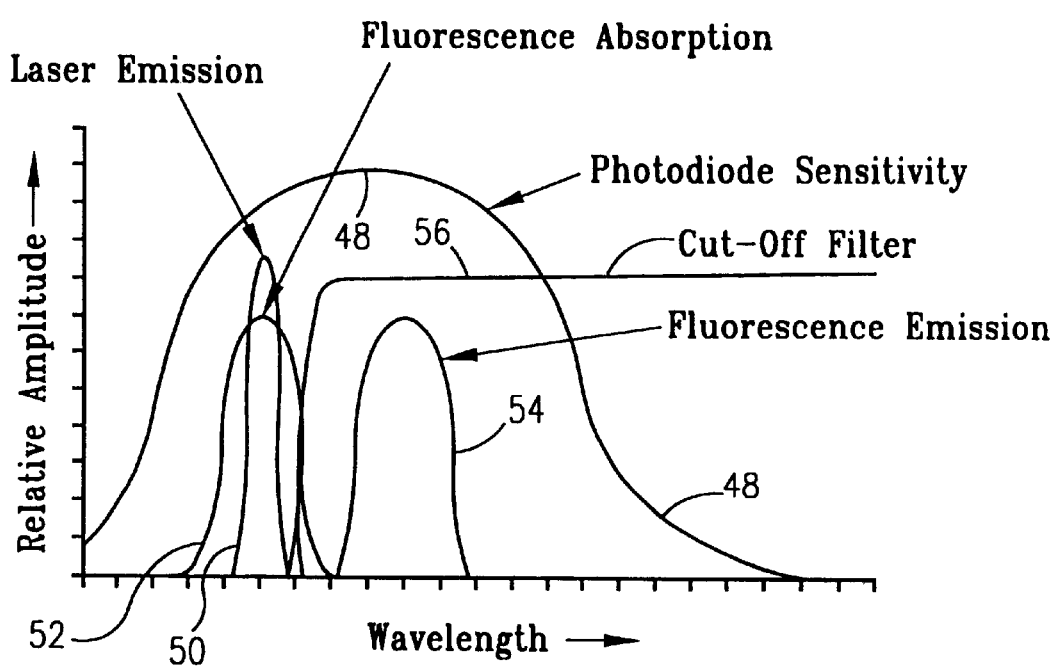

Referring to FIG. 7, the spectral response for the photodetector 22 is indicated at 48. The laser beam wavelength is generally indicated at 50. A fluorescence absorption wavelength band is generally indicated at 52. The fluorescence emission wavelength band is generally indicated at 54. The filter 40 is an optical cut-off filter that prevents light at the absorbance wavelength 52 from reaching the photodetectors, but permits any light due to fluorescence emission 54. The filter limits the exposure of the filtered photodetectors to those wavelengths longer than the filter cut-off wavelength, generally indicated at 56. The filter 40 may also be a bandpass filter.

Data from the filtered set of photodetectors are used to reconstruct a fluorescent image of areas within the breast. Fluorescence is introduced into the breast through use of a fluorophore, such as Indocynine Green or an appropriate contrast agent that is injected into the bloodstream or otherwise introduced into the breast. The fluorophore is excited by the laser source, causing it to emit fluorescent light. Data from the unfiltered row of photodetectors are used to reconstruct an absorption image of the breast. Since the perimeter of the breast is acquired during scanning of the breast, the absorption and fluorescent images, which are reconstructed using the unfiltered laser light and the fluorescent emission caused by the excitation of the fluorophore by the scanning laser beam, are automatically co-registered within the perimeter. Examples of means for acquiring the perimeter of the breast during scanning are disclosed in U.S. Pat. Nos. 6,044,288 and 6,029,077, incorporated herein by reference.

Use of a fluorophore is further disclosed in U.S. Pat. No. 5,952,664, issued on Sep. 14, 1999, which is hereby incorporated by reference.

Figure 8:
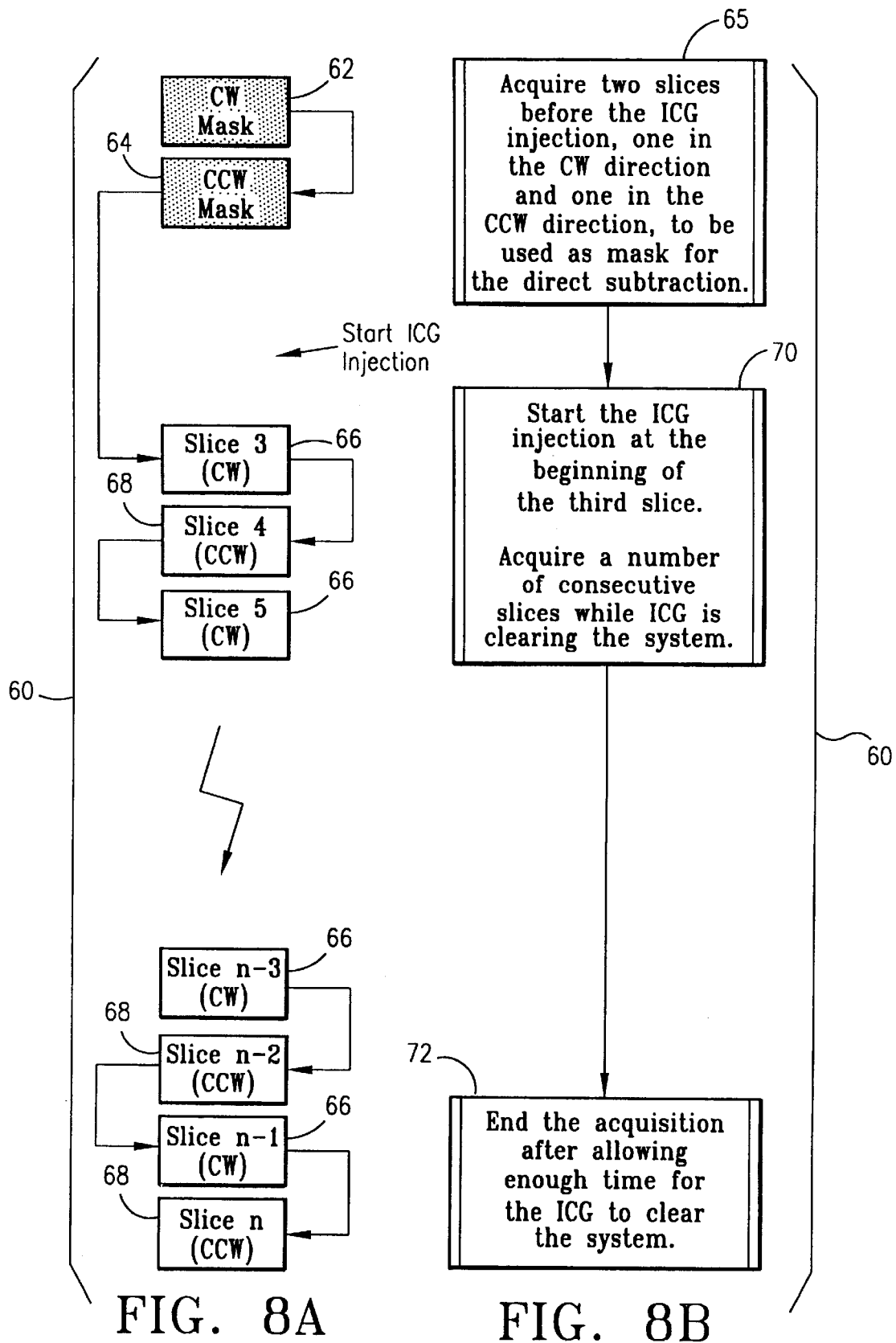
FIGS. 8A and 8B are flow diagrams showing data acquisition for mask data and projection data.

The digitized signals stored in the computer 30 is herein referred to as projection data, which are used to reconstruct an image of the breast, as disclosed in U.S. Pat. No. 6,130,958, hereby incorporated by reference. Referring to FIGS. 8A and 8B, a flow diagram for a series of projection data acquisitions is disclosed. The patient is positioned prone on the scanning table 4 with her breast 6 placed through the opening in the scanning chamber 18. The laser beam and photodetectors 22 are rotated together 360° in one direction around the breast and one set of projection data is acquired, corresponding to the upper and lower rows of detectors. At the completion of the acquisition, the direction of rotation of the scanner is reversed and another set of projection data are acquired corresponding to the upper and lower rows of detectors. This series of data acquisition is generally indicated at 60.

References to "mask" and "slice" in FIGS. 8A, 8B and 9 and below refer to the two sets of data simultaneously acquired by the upper and lower rows of photodetectors as the scanner is rotated in a clockwise or counterclockwise direction, where one set of data corresponds to the upper row of photodetectors scanning the breast through the plane 41, and the other set of data corresponds to the lower row of photodetectors scanning through the plane 43 (see FIG. 2).

To establish a pre-injection baseline, the first and second sets of projection data, referred to as clockwise(CW) mask 62 and counterclockwise(CCW) mask 64, respectively, are taken prior to the ICG injection, as indicated at 65. After the CW mask 62 and the CCW mask 64 are acquired, the scan continues at the same vertical position of the scanner with repeated acquisitions of projection data, with data acquired with a clockwise rotation being referred to as slice CW data 66 and the counterclockwise data as slice CCW data 68.

After the CW mask 62 and CCW mask 64 are taken, a contrast agent, such as Indocynine Green (ICG), is injected into the body, as generally indicated at 70. ICG is a standard diagnostic aid for blood flow measurements. Data acquisitions continue for a period of time, alternating between CW data 66 and CCW data 68 until the ICG clears the system, generally indicated at 72.

Figure 9:
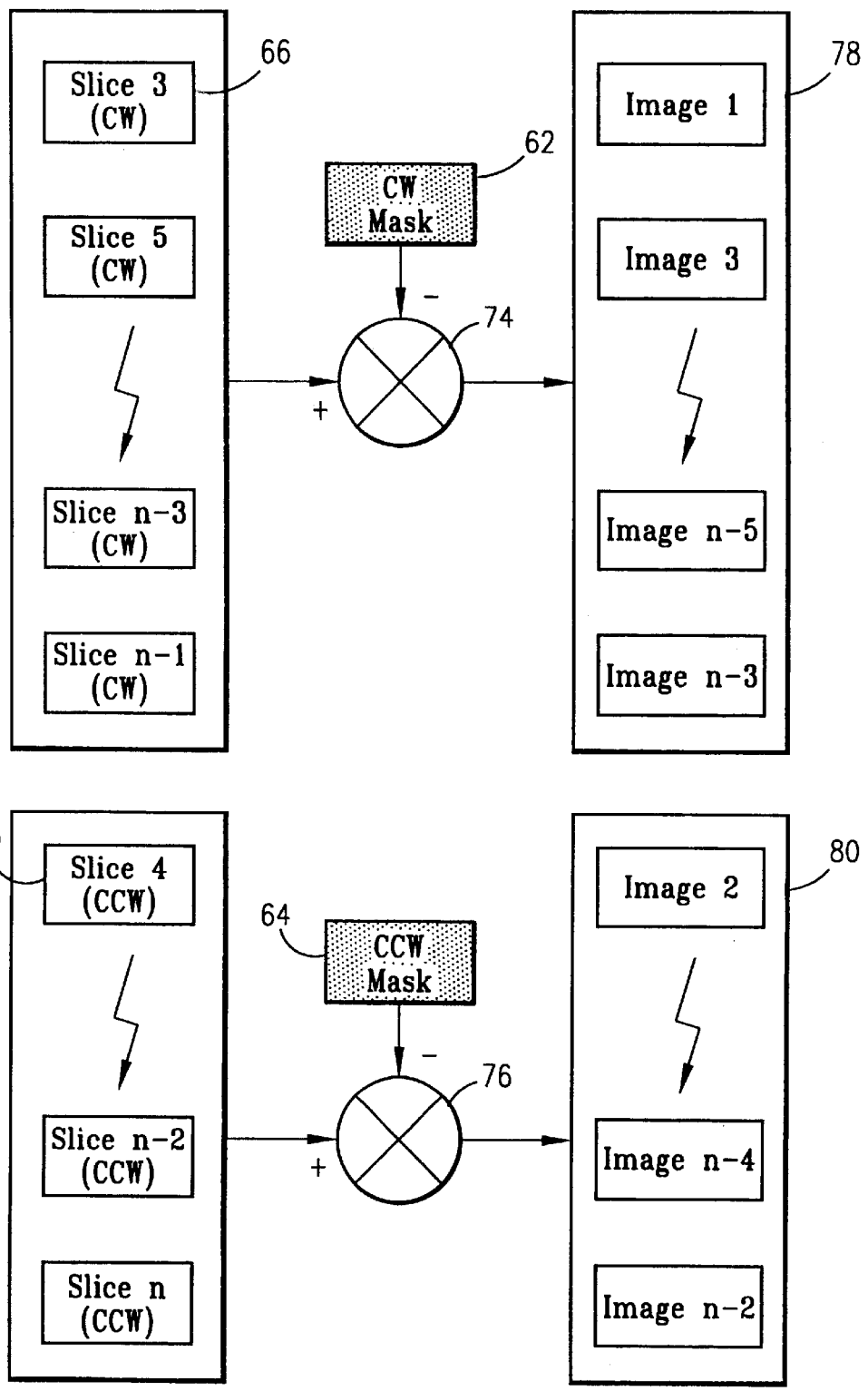
FIG. 9 is a flow diagram showing the subtraction of mask data from respective slice date projection prior to image reconstruction.

Referring to FIG. 9, after the data acquisition sequence is completed, data subtractions at 74 and 76 are performed prior to image reconstruction. Since optical image reconstruction algorithms are iterative that exhibit non-linear characteristics because of negativity and relaxation constraints, projection data are subtracted rather than the reconstructed images. For data acquired with clockwise rotation, slice data 66 and mask data 62 are used. Digital subtraction is performed with the mask data 62 being subtracted from the respective slice data 66 to derive image projection data to reconstruct images 78. Similarly, digital subtraction at 76 is performed with mask data 64 being subtracted from the respective slice data 68 to derive image projection data to reconstruct images 80. In the subtraction, it should be understood that the upper or lower row component of the mask data is subtracted from the respective upper or lower row component of the slice data. This subtraction process results in an image that contains only the information that is new in the images obtained after use of the contrast agent. A time-series of images of the breast are thereby created, showing fluorescent images as the ICG arrives and perfuses the breast, which may be used to demonstrate uptake, washout, etc. of the contrast agent.

In the data acquisition sequence described above, the scanner is stationary at a certain vertical position where the lesion in the breast is expected to exhibit the largest cross-sectional area through the slice plane.

Where the scanner 10 is used for a single wavelength, the filters 40 would be removed and the mask data would not be obtained, since subtraction would not be performed.

In addition to photodiodes, the photodetectors 22 may also be avalanche photodiodes, photo-multiplier tubes, micro-channel plates, charged coupled devices (CCD) or other photodetectors.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. An apparatus for imaging a breast, comprising:
   a) a scanning chamber for receiving therein the breast to be scanned;
   b) a laser beam disposed within said scanning chamber for impinging on the breast, said laser beam being adapted to orbit around the breast;
   c) first and second groups of detectors positioned in an arc around the breast to simultaneously detect light emerging from the breast to generate first and second projection data, respectively;
   d) optical filters operably associated with said first group of detectors to restrict the wavelength of light reaching said first group of detectors to the wavelength of radiation emitted by a contrast agent introduced into the breast after being activated by said beam; and
   e) a computer to reconstruct an image of the breast from projection data derived from subtracting first and second baseline projection data prior to introduction of the contrast agent into the breast from respective first and second projection data obtained after introduction of the contrast agent.

2. An apparatus as in claim 1, wherein said first baseline projection data is obtained from said first and second groups of detectors during a clockwise rotation thereof.

3. An apparatus as in claim 1, wherein said second baseline projection data is obtained from said first and second groups of detectors during a counterclockwise rotation thereof.

4. An apparatus as in claim 1, wherein said filters are cut-off filters.

5. A detector array as in claim 1, wherein said filters are band pass filters.

6. A detector array as in claim 1, wherein said first and second groups of detectors are arranged in respective first and second rows.

7. A detector array as in claim 1, wherein:
   a) said first row is disposed above said second row; and
   b) said first row is parallel to said second row.

8. An apparatus as in claim 1, wherein said first row is horizontally offset from said second row.

* * * * *